(12) United States Patent
Hojo

(10) Patent No.: US 9,643,908 B2
(45) Date of Patent: May 9, 2017

(54) FRAGRANCE COMPOSITION

(71) Applicant: TAKASAGO INTERNATIONAL CORPORATION, Tokyo (JP)

(72) Inventor: Kazuma Hojo, Chigasaki (JP)

(73) Assignee: TAKASAGO INTERNATIONAL CORPORATION, Tokyo (JP)

( * ) Notice: Subject to any disclaimer, the term of this patent is extended or adjusted under 35 U.S.C. 154(b) by 0 days.

(21) Appl. No.: 14/914,026

(22) PCT Filed: Sep. 8, 2014

(86) PCT No.: PCT/JP2014/073670
§ 371 (c)(1),
(2) Date: Feb. 24, 2016

(87) PCT Pub. No.: WO2015/034084
PCT Pub. Date: Mar. 12, 2015

(65) Prior Publication Data
US 2016/0207862 A1 Jul. 21, 2016

(30) Foreign Application Priority Data

Sep. 6, 2013 (JP) .................................. 2013-185114

(51) Int. Cl.
| | |
|---|---|
| C07C 49/11 | (2006.01) |
| A61K 8/35 | (2006.01) |
| A61Q 13/00 | (2006.01) |
| C11B 9/00 | (2006.01) |
| A61Q 5/02 | (2006.01) |
| A61Q 19/10 | (2006.01) |
| C11D 3/20 | (2006.01) |

(52) U.S. Cl.
CPC ................ *C07C 49/11* (2013.01); *A61K 8/35* (2013.01); *A61Q 5/02* (2013.01); *A61Q 13/00* (2013.01); *A61Q 19/10* (2013.01); *C11B 9/003* (2013.01); *C11D 3/2072* (2013.01); *C07C 2101/08* (2013.01)

(58) Field of Classification Search
IPC .................... A61K 8/35; C07C 49/11
See application file for complete search history.

(56) References Cited

U.S. PATENT DOCUMENTS

| | | | | |
|---|---|---|---|---|
| 4,052,341 A | * | 10/1977 | Naipawer | ............... C07C 45/58 512/2 |
| 8,030,524 B2 | | 10/2011 | Bajgrowicz | |
| 2008/0138482 A1 | | 6/2008 | Mane et al. | |
| 2010/0069508 A1 | | 3/2010 | Bajgrowicz | |

FOREIGN PATENT DOCUMENTS

| | | | |
|---|---|---|---|
| CN | 1101125798 | * | 5/2010 |
| JP | 2010-508310 A | | 3/2010 |
| JP | 2010-511677 A | | 4/2010 |
| JP | 2013-147448 A | | 8/2013 |
| JP | 2013-256470 A | | 12/2013 |
| WO | 01/85883 A1 | | 11/2001 |
| WO | WO 2008/068310 | * | 6/2008 |

OTHER PUBLICATIONS

Linhua Zhang et al., Factors influencing the quality of synthetic sandalwood 3-methyl-5-(2,2,3-trimethylcyclopent-3-en-l-yl) pentan-2-ol, Huaxue Tongbao, 1988, pp. 39-40, vol. 10, ISSN: 0441-3776.
International Searching Authority International Search Report for PCT/JP2014/073670 dated Nov. 25, 2014.

* cited by examiner

Primary Examiner — Shirley V Gembeh
(74) Attorney, Agent, or Firm — Sughrue Mion, PLLC

(57) ABSTRACT

The present invention provides a compound represented by the following general formula (A)

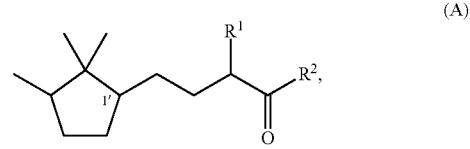

(A)

wherein 1'-position is optically active; and one of R1 and R2 represents a methyl group and the other represents an ethyl group, or both R1 and R2 represent a methyl group.

17 Claims, No Drawings

FRAGRANCE COMPOSITION

CROSS REFERENCE TO RELATED APPLICATIONS

This application is a National Stage of International Application No. PCT/JP2014/073670 filed Sep. 8, 2014, claiming priority based on Japanese Patent Application No. 2013-185114 filed Sep. 6, 2013, the contents of all of which are incorporated herein by reference in their entirety.

TECHNICAL FIELD

The present invention relates to an optically active ketone compound, a fragrance composition containing the compound as an active ingredient, and products such as cosmetics containing the compound as an active ingredient.

BACKGROUND ART

In our modern life, various products having preferable odors have been available on the market. However, there has been a demand for a wider variety of scented products, and provision of a highly preferable odor has been required. For example, it is generally known that compounds having a cyclopentane ring have a sandalwood-like odor or a woody-amber, and many such compounds have been developed.

For example, Huaxue Tongbao, 1988, vol. 10, p. 39 states that 3-methyl-5-(2,2,3-trimethyl-3-cyclopenten-1-yl)pentanol has a strong sandalwood-like odor.

SUMMARY OF INVENTION

Huaxue Tongbao, 1988, vol. 10, p. 39 describes the odor notes of three related compounds of the above-described compound such as a ketone derivative. However, the odor of each of the three related compounds is evaluated to be unpleasant or very weak, and the odor is not so highly regarded. In addition, each of these compounds is a racemate, and neither stereoisomers of each of the compounds nor the odors of the stereoisomers are described at all.

The present inventors have examined the odors of the stereoisomers of 3-methyl-5-(2,2,3-trimethylcyclopentan-1-yl)-2-pentanone and analogues thereof, which are described to have very weak odors, and consequently found that optically active 1'R isomers have a pleasant strong musk odor with good diffusibility. This finding has led to the completion of the present invention.

The present invention includes the following inventions (1) to (12).
(1) A compound represented by the following general formula (A)

(A)

wherein 1'-position is optically active; and one of R1 and R2 represents a methyl group and the other represents an ethyl group, or both R1 and R2 represent a methyl group.
(2) The compound according to the above-described item 1, wherein
the optical purity regarding a configuration at 1'-position is in a range from 20% e.e. to 99% e.e, and R1 and R2 are methyl groups.
(3) The compound according to the above-described item 1, wherein
one of R1 and R2 is a methyl group, and the other is an ethyl group.
(4) The compound according to any one of the above-described items 1 to 3, wherein
an R-isomer is in excess regarding the optical activity at 1'-position in formula (A).
(5) An optically active (1'R)-3-methyl-5-(2,2,3-trimethylcyclopentan-1-yl)-2-pentanone, wherein
the optical purity regarding a configuration at 1'-position is in a range from 20% e.e. to 99% e.e.
(6)
(1'R)-3-Methyl-5-(2,2,3-trimethylcyclopentan-1-yl)-2-pentanone.
(7) A fragrance composition comprising the compound according to any one of the above-described items 1 to 6.
(8) The fragrance composition according to the above-described item 7, wherein
the content of the compound according to any one of the above-described items 1 to 6 is 0.01 to 60% by weight.
(9) The fragrance composition according to the above-described item 7 or 8, wherein.
the chemical purity of the compound is 80% or higher.
(10) A product scented with the fragrance composition according to any one of the above-described items 7 to 9.
(11) The scented product according to the above-described item 10, which is one selected from fragrance products, cosmetics, basic skin care cosmetics, make-up cosmetics, hair cosmetics, sunscreen cosmetics, medicated cosmetics, hair-care products, soaps, body cleaning agents, bath agents, laundry detergents, finishing softeners for clothes, cleaning agents, kitchen detergents, bleaching agents, aerosols, air fresheners, repellents, and groceries.
(12) A method for augmenting or modifying an odor of a fragrance composition, the method comprising adding the compound according to the above-described items 1 to 6.

The addition of the compound of the present invention in which the R-isomer is in excess regarding the optical activity at 1'-position in formula (A), especially, optically active (1'R)-3-methyl-5-(2,2,3-trimethylcyclopentan-1-yl)-2-pentanone whose optical purity regarding the configuration at 1'-position is in a range from 20% e.e. to 99% e.e. makes it possible to obtain a fragrance composition with a characteristic odor having good diffusibility. This composition is widely used as a fragrance or a composition for scenting cosmetics, sanitary and hygiene materials, and the like.

Meanwhile, a compound of the present invention in which the S-isomer is in excess can be used for obtaining a desired optical purity by mixing this compound with the corresponding R-isomer of the compound and thus obtaining a fragrance composition with an excellent odor.

DESCRIPTION OF EMBODIMENTS

Hereinafter, the present invention will be described in detail.

The present invention provides a compound represented by the following general formula (A):

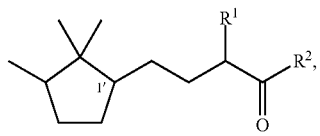

(A)

wherein 1'-position is optically active; and one of R1 and R2 represents a methyl group and the other represents an ethyl group, or both R1 and R2 represent a methyl group.

In the above-described formula (A), the optical purity regarding the configuration at 1'-position is preferably in a range from 20% e.e. to 99% e.e. In addition, an R-isomer is preferably in excess regarding the optical activity at 1'-position.

Preferred examples of the compound of formula (A) of the present invention include the following compounds:
(1'R)-3-methyl-(2,2,3-trimethylcyclopentan-1-yl)-2-pentanone;
(1'S)-3-methyl-5-(2,2,3-trimethylcyclopentan-1-yl)-2-pentanone;
(1'R)-3-ethyl-5-(2,2,3-trimethylcyclopentan-1-yl)-2-pentanone;
(1'S)-3-ethyl-5-(2,2,3-trimethylcyclopentan-1-yl)-2-pentanone;
(1'R)-4-methyl-6-(2,2,3-trimethylcyclopentan-1-yl)-3-hexanone; and
(1'S)-4-methyl-6-(2,2,3-trimethylcyclopentan-1-yl)-3-hexanone.

The compound of the present invention is preferably optically active (1'R)-3-methyl-5-(2,2,3-trimethylcyclopentan-1-yl)-2-pentanone (the following compound (1)) whose optical purity regarding the configuration at 1'-position is in a range from 20% e.e. to 99% e.e. By taking this compound as an example, the present invention will be described in further detail.

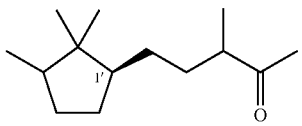

(1)

The above-described compound (1) whose optical purity regarding the configuration at 1'-position is 20% e.e. to 99% e.e. has a musk-like odor with diffusibility. The optical purity regarding the configuration at 1'-position is further preferably in a range from 60% e.e. to 99% e.e. Compounds whose optical purities regarding the configuration at 1'-position are out of this range are poor in odor and cannot be said to be sufficient in terms of odor. The optical purity can be determined by, for example, NMR and/or any of various chromatographic techniques using a chiral column.

In addition, the chemical purity of the above-described compound (1) only needs to be 80% or higher, and is preferably 90% or higher.

As the above-described compound (1) used in the present invention, one obtained by a chemical synthesis method can be used. For example, the compound (1) is synthesized by a method shown below (Scheme 1); however, the synthesis of compound (1) is not limited to the following method.

(Scheme 1)

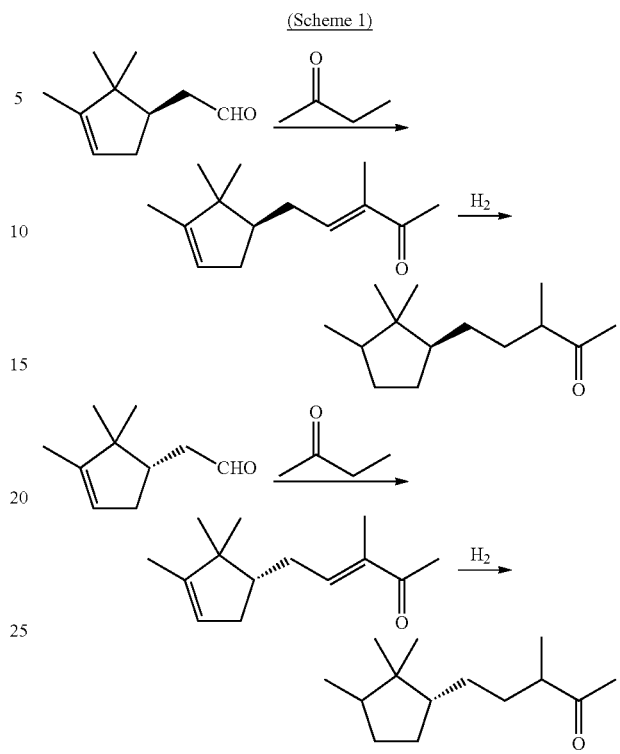

Specifically, (R)- or (S)-2-(2,2,3-trimethyl-3-cyclopentenyl)acetaldehyde is reacted with 2-butanone in the presence of a base to obtain an unsaturated ketone. Subsequently, the carbon-carbon double bonds are hydrogenated by using a catalyst such as Pd/C. Thus, optically active (1'R)- or (1'S)-3-methyl-5-(2,2,3-trimethylcyclopentan-1-yl)-2-pentanone can be obtained. Mixing two isomers obtained in this manner makes it possible to obtain (1'R)-3-methyl-5-(2,2,3-trimethylcyclopentan-1-yl)-2-pentanone of the present invention whose optical purity regarding the configuration at 1'-position is within the specific range.

Alternatively, the (1'R)-3-methyl-5-(2,2,3-trimethylcyclopentan-1-yl)-2-pentanone of the present invention whose optical purity regarding the configuration at 1'-position is within the specific range can be obtained without the mixing operation, when the optical purity at the corresponding position of the starting substance, 2-(2,2,3-trimethyl-3-cyclopenten-1-yl) acetaldehyde, is already within the specific range of the optical purity regarding the configuration at 1'-position of (1'R)-3-methyl-5-(2,2,3-trimethylcyclopentan-1-yl)-2-pentanone of the present invention.

Other compounds of the present invention can also be obtained by reacting (R)- or (S)-2-(2,2,3-trimethyl-3-cyclopentenyl) acetaldehyde with corresponding ketones in the same manner as described above.

A fragrance composition can be obtained by using the compound of the present invention as an active ingredient. The amount of the compound of the present invention, for example, the optically active (1'R)-3-methyl-5-(2,2,3-trimethylcyclopentan-1-yl)-2-pentanone whose optical purity regarding the configuration at 1'-position is within the specific range formulated in the fragrance composition is not particularly limited, and is preferably 0.01 to 60% by weight and particularly preferably 0.1 to 40% by weight relative to the fragrance composition.

In addition, one or more generally used additional fixatives may be formulated. For example, it is also possible to use the compound of the present invention in combination with ethylene glycol, propylene glycol, dipropylene glycol, glycerin, hexylene glycol, benzyl benzoate, triethyl citrate, diethyl phthalate, Hercolyn, medium-chain fatty acid triglyceride, or the like.

In the fragrance composition of the present invention, any generally used compound perfume can be formulated. A fragrance composition thus obtained makes it possible to impart a fresh and highly-preferred odor. In addition, the fragrance composition of the present invention can impart its unique odor to, for example, fragrance products, cosmetics, basic skin care cosmetics, make-up cosmetics, hair cosmetics, sunscreen cosmetics, medicated cosmetics, hair-care products, soaps, body cleaning agents, bath agents, laundry detergents, finishing softeners for clothes, cleaning agents, kitchen detergents, bleaching agents, aerosols, air fresheners, repellents, and groceries by formulating the fragrance composition of the present invention as a fragrance component in amounts generally formulated in their industrial fields to increase the values of these products.

Examples of the fragrance products include perfume, Eau de Parfum, Eau de Toilette, Eau de Cologne, and the like. Examples of the basic skin care cosmetics include face wash creams, vanishing creams, cleansing creams, cold creams, massage creams, emulsions, lotions, cosmetic serums, packs, make-up removers, and the like. Examples of the make-up cosmetics include foundations, lipsticks, lip balms, and the like. Examples of the hair cosmetics include hair tonics, hair lotions, hair sprays, and the like. Examples of the sunscreen cosmetics include suntan products, sunscreen products, and the like. Examples of the medicated cosmetics include antiperspirants, after-shaving lotions and gels, permanent wave agents, medicated soaps, medicated shampoos, medicated skin cosmetics, and the like.

The hair-care products include shampoos, rinses, two-in-one shampoos, conditioners, treatments, hair packs, and the like. The soaps include toilet soaps, bath soaps, and the like. The body cleaning agents include body soaps, body washes, hand soaps, and the like. The bath agents include bath additives (bath salts, bath tablets, bath liquids, and the like), foam baths (bubble baths and the like), bath oils (bath perfumes, bath capsules, and the like), milk baths, bath jellies, bath cubes, and the like.

The detergents include heavy duty detergents for clothes, light duty detergents for clothes, liquid detergents, laundry soaps, compact detergents, powder soaps, and the like. The finishing softeners include softeners, furniture cares, and the like. The cleaning agents include cleansers, house cleaning agents, toilet cleaning agents, bath room cleaning agents, glass cleaners, mold removers, drainpipe cleaning agents, and the like. The kitchen detergents include kitchen soaps, kitchen synthetic soaps, dish detergents, and the like. The bleaching agents include oxidation-type bleaching agents (chlorine-based bleaching agents, oxygen-based bleaching agents, and the like), reduction-type bleaching agents (sulfur-based bleaching agents and the like), optical bleaching agents, and the like. The aerosols include spray-type aerosols, powder sprays, and the like. The air fresheners include solid-type air fresheners, gel-type air fresheners, liquid-type air fresheners, and the like. The groceries may be in various forms such as tissue paper, toilet paper, and the like.

When the fragrance composition of the present invention is used in any of the above-described products, the fragrance composition is used in any form selected according to the purpose. Specifically, the fragrance composition of the present invention may be used as it is. Alternatively, the fragrance composition of the present invention may be used in a liquid state achieved by dissolving the fragrance composition in, for example, an alcohol or a polyol such as propylene glycol or glycerin, in a solubilized or dispersed state achieved by solubilizing or dispersing the fragrance composition by using a surfactant, for example, a nonionic surfactant, an anionic surfactant, a cationic surfactant, an amphoteric surfactant, or the like, in a microcapsule state achieved by treating the fragrance composition with an encapsulating agent; or in other states.

Moreover, in some cases, the fragrance composition of the present invention may be used using a stabilized and sustained-release form by forming an inclusion compound in an agent for inclusion such as cyclodextrin. These are suitable for the forms of finished products such as, for example, liquid forms, solid forms, powder forms, gel forms, mist forms, and aerosol forms, and are selectively used as appropriate.

Note that the amounts of the optically active (1'R)-3-methyl-5-(2,2,3-trimethylcyclopentan-1-yl)pentan-2-one of the present invention whose optical purity regarding the configuration at 1'-position is within the specific range added to the finished products such as fragrance products, cosmetics, basic skin care cosmetics, make-up cosmetics, hair cosmetics, sunscreen cosmetics, medicated cosmetics, hair-care products, soaps, body cleaning agents, bath agents, detergents, finishing softeners, cleaning agents, kitchen detergents, bleaching agents, aerosols, air fresheners, repellents, and groceries may be increased or decreased to any amounts according to effects and actions expected in individual cases.

EXAMPLES

Hereinafter, the present invention is described specifically based on Examples etc. However, the present invention is not limited to these Examples etc. at all. Note that measurements in Examples were carried out using the following instruments.

NMR spectrometer ($^1$H-NMR, $^{13}$C-NMR): AVANCE III Model 500 (500 MHz; manufactured by Bruker BioSpin K.K.) Internal standard substance: $CDCl_3$ Gas chromatograph/mass spectrometer (GC/MS) GCMS-QP2010 Ultra (manufactured by Shimadzu Corporation)

Column used: BC-WAX (50 m in length×0.25 mm in inner diameter, liquid phase film thickness: 0.15 μm, manufactured by GL Sciences Inc.)

Gas chromatography (GC, chemical purity): GC-4000 (manufactured by GL Sciences Inc.)

Column used: InertCap 1 (30 m in length×0.25 mm in inner diameter, liquid phase film thickness: 0.25 μm, manufactured by GL Sciences Inc.)

Gas chromatography (GC, optical purity and isomer ratio): GC-2010 (manufactured by Shimadzu Corporation)

Column used: β-DEX325 (30 min length×0.25 mm in inner diameter, liquid phase film thickness: 0.25 μm, manufactured by SUPELCO)

Polarimeter: P-1020 (manufactured by JASCO Corporation)

Infrared absorption spectrometer: NICOET iS10 (manufactured by Thermo Scientific)

Example 1

Synthesis of (1'R)-3-methyl-5-(2,2,3-trimethylcyclopentan-1-yl)-2-pentanone

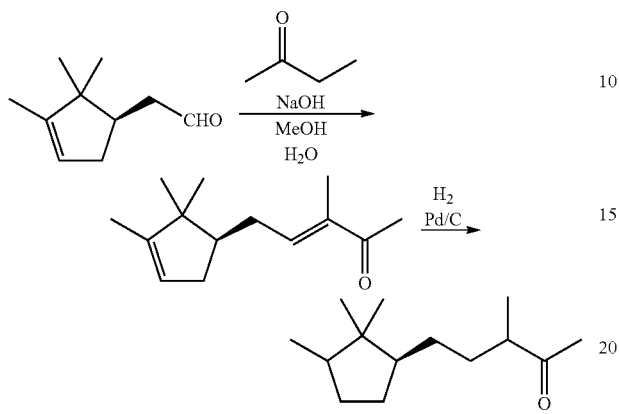

Under a nitrogen stream, a mixture solution of methanol (37 ml), sodium hydroxide (1.9 g, 0.048 mol), and water (4.0 ml) was stirred with ice-cooling. To this solution, 2-butanone (17.3 g, 0.24 mol) was slowly added dropwise, followed by stirring for 15 minutes. Then, (R)-2-(2,2,3-trimethyl-3-cyclopenten-1-yl) acetaldehyde (82% e.e., 18.3 g, 0.12 mol) was added dropwise over 1 hour so slowly that the temperature was kept at 0 to 10° C. After the stirring was continued for 20 hours with the temperature kept at 0 to 10° C., the mixture was heated to 40° C. and further stirred for 3 hours. After the reaction solution was cooled to room temperature, methanol and the remaining 2-butanone were recovered under reduced pressure. After water was added, extraction with toluene was carried out. After that, the obtained organic layer was washed with 10% aqueous sodium chloride and water, and then dried over sodium sulfate. After the solvent was evaporated under reduced pressure, the obtained crude product was purified by silica gel chromatography (hexane/ethyl acetate=19/1) to obtain (1'R)-3-methyl-5-(2,2,3-trimethylcyclopenten-1-yl)-3-penten-2-one (15.2 g, 0.074 mol, purity: 85.4%) as a pale yellow oily substance. Percentage yield: 52%.

Next, (1'R)-3-methyl-5-(2,2,3-trimethylcyclopenten-1-yl)-3-penten-2-one (12.5 g, 0.061 mol, purity: 85.4%) and 5% Pd/C (0.13 g) were placed in a 100 ml autoclave, and the reaction was allowed to proceed under a hydrogen pressure of 2.5 MPa at 80° C. for 2 hours. After cooling to room temperature, the catalyst was filtered off, and the obtained crude product was purified by silica gel chromatography (hexane/ethyl acetate=19/1) to obtain (1'R)-3-methyl-5-(2,2,3-trimethylcyclopentan-1-yl)-2-pentanone (9.7 g, 0.046 mol) as a colorless oily substance. Percentage yield: 89%. The optical purity was 82 e.e.

GC/MS (m/e): 210 (M$^+$, 5%), 192 (3), 167 (2), 153 (3), 138 (5), 123 (7), 109 (7), 85 (10), 72 (100), 69 (25), 43 (20), 41 (10); $^1$H NMR (CDCl$_3$, 500 MHz) δ 0.48 (d, 3H, J=5.4 Hz), 0.82 (dd, 3H, J=6.8, 1.2 Hz), 0.84 (s, 3H), 0.92-1.02 (m, 1H), 1.08 (t, 3H, J=7.0 Hz), 1.12-1.17 (m, 1H), 1.18-1.27 (m, 1H), 1.29-1.33 (m, 1H), 1.34-1.43 (m, 1H), 1.49-1.51 (m, 1H), 1.52-1.58 (m, 1H), 1.66-1.76 (m, 2H), 1.77-1.85 (m, 11-1), 2.13 (d, 3H, J=3.8 Hz), 2.50 (m, 1H);
$^{13}$C NMR (CDCl$_3$, 500 MHz) δ 212.86, 212.82, 50.98, 50.73, 47.63, 47.42, 45.17, 42.26, 32.36, 32.02, 30.06, 28.17, 28.13, 27.91, 27.88, 27.86, 25.61, 25.60, 16.44, 15.88, 14.32, 13.79;

Specific rotation [α]$^{20}$: +24.7 (neat);
IR (ATR, diamond cell was used, cm$^{-1}$): 2953, 2868, 1715, 1458, 1386, 1365, 1162.
Odor description: strong musk, transparent and warm odor.

Example 2

Synthesis of (1'S)-3-methyl-(2,2,3-trimethylcyclopentan-1-yl)-2-pentanone

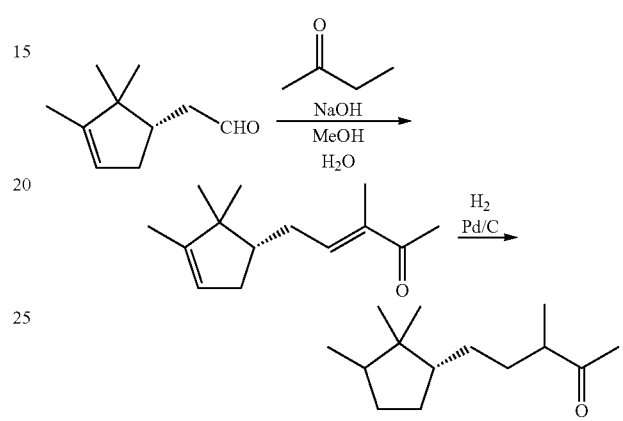

By using (S)-2-(2,2,3-trimethyl-3-cyclopenten-1-yl)acetaldehyde (55% e.e.) instead of (R)-(2,2,3-trimethyl-3-cyclopenten-1-yl)acetaldehyde used in Example 1, (1'S)-3-Methyl-5-(2,2,3-trimethylcyclopentan-1-yl)-2-pentanone was synthesized by the same method as In Example 1. The optical purity was 55% e.e.

GC/MS (m/e): 210 (M$^+$, 5%), 192 (2), 167 (2), 153 (3), 138 (5), 123 (7), 109 (7), 85 (10), 72 (100), 69 (25), 43 (20), 41 (10); $^1$H NMR (CDCl$_3$, 500 MHz) δ 0.48 (d, 3H, J=5.4 Hz), 0.82 (dd, 3H, J=6.8, 1.2 Hz), 0.84 (s, 3H), 0.92-1.02 (m, 1H), 1.08 (t, 3H, J=7.0 Hz), 1.12-1.17 (m, 1H), 1.18-1.27 (m, 1H), 1.29-1.33 (m, 1H), 1.34-1.43 (m, 1H), 1.49-1.51 (m, 1H), 1.52-1.58 (m, 1H), 1.66-1.76 (m, 2H), 1.77-1.85 (m, 1H), 2.13 (d, 3H, J=3.9 Hz), 2.50 (m, 1H);
$^{13}$C NMR (CDCl$_3$, 500 MHz) δ 212.93, 212.89, 50.98, 50.73, 47.65, 47.43, 45.17, 42.27, 32.37, 32.02, 30.06, 28.17, 28.14, 27.91, 27.90, 27.87, 25.62, 25.61, 16.45, 15.88, 14.33, 13.81;
Specific rotation [α]$^{20}$: −17.0 (neat);
IR (AIR, diamond cell was used, cm$^{-1}$): 2950, 2867, 1713, 1458, 1364, 1162.
Odor description: woody, fruity, and faintly metallic.

Example 3

Synthesis of (1'R)-3-ethyl-5-(2,2,3-trimethylcyclopentan-1-yl)-2-pentanone

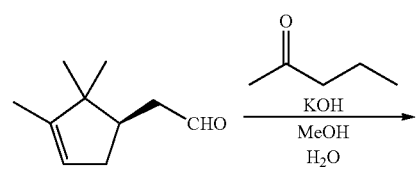

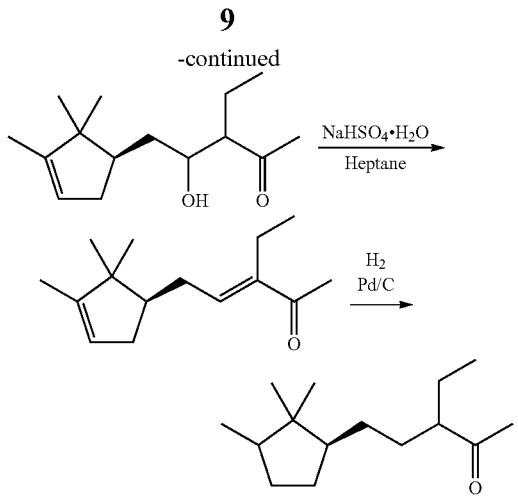

Under a nitrogen stream, a mixture solution of methanol (47.7 ml), 96% potassium hydroxide (9.2 g, 0.16 mol), and water (47.7 ml) was stirred with ice-cooling. To this mixture, 2-pentanone (84.8 g, 0.98 mol) was slowly added dropwise, followed by stirring for 15 minutes. After that, (R)-2-(2,2,3-trimethyl-3-cyclopenten-1-yl)acetaldehyde (82% e.e., 47.7 g, 0.31 mol) was added dropwise over 30 minutes so slowly that the temperature was kept at 0 to 10° C. After the stirring was continued for 7.5 hours with the temperature kept at 0 to 10° C., methanol was recovered under reduced pressure. After addition of water and extraction with toluene, the obtained organic layer was washed with 10% aqueous sodium chloride and water, and then the solvent was evaporated under reduced pressure to obtain a crude product of (1'R)-3-ethyl-4-hydroxy-5-(2,2,3-trimethylcyclopenten-1-yl)-2-pentanone. To a 200 ml three-necked flask equipped with a thermometer, a Dean-Stark trap, and a Dimroth condenser, all the crude product of (1'R)-3-ethyl-4-hydroxy-5-(2,2,3-trimethylcyclopenten-1-yl)-2-pentanone, sodium hydrogen sulfate monohydrate (0.67 g, 4.9 mmol), and heptane (34 ml) were added, and heated under reflux. The mixture was stirred for 1 hour, while water produced by dehydration was taken out on an as needed basis through the Dean-Stark trap to the outside of the system. After being cooled to room temperature, the reaction solution was washed sequentially with a 10% aqueous sodium carbonate solution and with saturated aqueous sodium chloride, and heptane was evaporated under reduced pressure. The obtained crude product was distilled under reduced pressure (83.2° C. to 84.2° C./69 Pa) to obtain (1'R)-3-ethyl-5-(2,2,3-trimethylcyclopenten-1-yl)-3-penten-2-one (35.5 g, 0.16 mol, purity: 65.3%) as a pale yellow oily substance. Percentage yield: 34%.

Next, (1'R)-3-ethyl-5-(2,2,3-trimethylcyclopenten-1-yl)-3-penten-2-one (10.0 g, 0.045 mol, purity: 65.3%), 5% Pd/C (0.10 g), and toluene (2.0 ml) were placed in a 100 ml autoclave, and the reaction was allowed to proceed at 100° C. for 1.5 hours at a Hydrogen pressure of 2.5 MPa. After cooling to room temperature, the catalyst was filtered, and the obtained crude product was purified by silica gel chromatography (hexane/ethyl acetate=19/1) to obtain (1'R)-3-ethyl-5-(2,2,3-trimethylcyclopentan-1-yl)-2-pentanone (4.4 g, 0.020 mol) as a colorless oily substance. Percentage yield: 66%. The optical purity was 82% e.e.

GC/MS (m/e) 224 (M+, 7%), 206 (3), 191 (6), 177 (3), 153 (4), 138 (4), 123 (7), 99 (12), 86 (100), 71 (30), 69 (40), 43 (60), (35);

$^1$H NMR (CDCl$_3$, 500 MHz) δ 0.47 (d, 3H, J=5.7 Hz), 0.82 (d, 3H, J=6.8 Hz), 0.84 (s, 3H), 0.84-0.88 (m, 3H), 0.90-1.01 (m, 1H), 1.06-1.21 (m, 2H), 1.27-1.37 (m, 3H), 1.43-1.54 (m, 3H), 1.56-1.65 (m, 1H), 1.69-1.83 (m, 2H), 2.11 (d, 3H, 4.9 Hz), 2.33-2.40 (m, 1H);

$^{13}$C NMR (CDCl$_3$, 500 MHz) δ 213.10, 213.02, 55.21, 50.99, 50.90, 45.18, 42.29, 42.26, 30.61, 30.47, 30.07, 28.67, 28.37, 28.23, 28.22, 28.19, 28.11, 25.62, 24.83, 24.30, 14.34, 13.82, 11.83, 11.73;

Specific rotation [α]$^{20}$ +22.7 (neat);

IR (AIR, diamond cell was used, cm$^{-1}$): 2951, 2867, 1712, 1457, 1365, 1351, 1160.

Odor description: musky, powdery, and milky odor with sweetness.

Example 4

Synthesis of (1'R)-4-methyl-6-(2,2,3-trimethylcyclopentan-1-yl)-3-hexanone

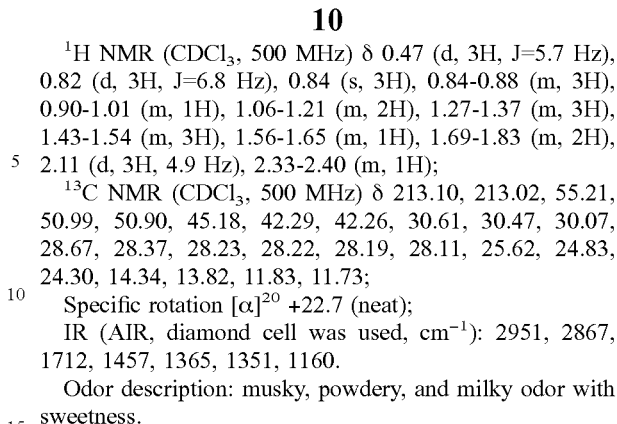

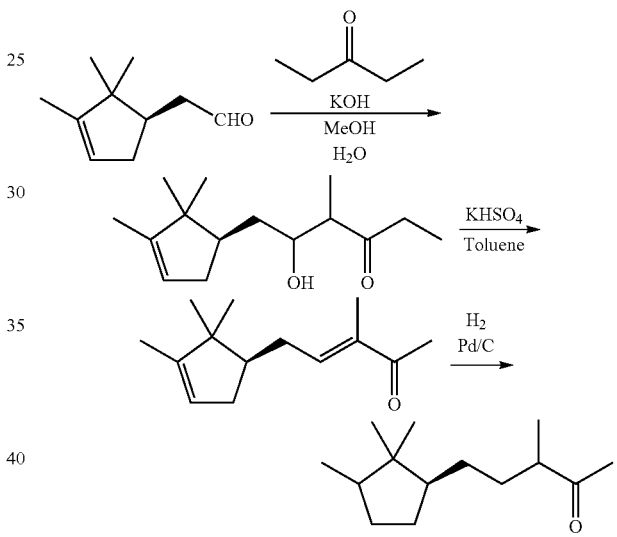

Under a nitrogen stream, a mixture solution of methanol (128 ml), 96% potassium hydroxide (8.9 g, 0.15 mol), and water (85.0 ml) was stirred with ice-cooling. To this mixture solution, 3-pentanone (71.2 g, 0.83 mol) was slowly added dropwise, followed by stirring for 15 minutes. After that, (R)-2-(2,2,3-trimethyl-3-cyclopenten-1-yl)acetaldehyde (82% e.e., 42.5 g, 0.28 mol) was added dropwise over 30 minutes so slowly that the temperature was kept at 0 to 10° C. After the mixture was stirred for 16 hours with the temperature kept at 0 to 10° C., methanol was recovered under reduced pressure. After addition of water and extraction with ethyl acetate, the obtained organic layer was washed with 10% aqueous sodium chloride and water, and then the solvent was evaporated under reduced pressure to obtain a crude product of (1'R)-5-hydroxy-4-methyl-6-(2,2,3-trimethylcyclopenten-1-yl)-3-hexanone. To a 300 ml three-necked flask equipped with a thermometer, a Dean-Stark trap, and a Dimroth condenser, all the crude product of (1'R)-5-hydroxy-4-methyl-6-(2,2,3-trimethylcyclopenten-1-yl)-3-hexanone, potassium hydrogen sulfate (1.9 g, 0.014 mol), and toluene (195 ml) were added, and heated under reflux. The mixture was stirred for 6 hours, while water produced by dehydration was taken out on an as needed basis through the Dean-Stark trap to the outside of the system. After being cooled to room temperature, the reaction solution was washed sequentially with a 10% aqueous sodium carbonate solution and with saturated aqueous sodium chloride, and toluene was evaporated under reduced pressure. The obtained crude product was distilled under reduced pressure (73.5° C. to 76.5° C./17 Pa) to obtain (1'R)-4-methyl-6-(2,2,3-trimethylcyclopenten-1-yl)-4-hexen-3-one (36.0 g, 0.16 mol, purity: 92.2%) as a pale yellow oily substance. Percentage yield: 54%.

Next, (1'R)-4-methyl-6-(2,2,3-trimethylcyclopenten-1-yl)-4-hexen-3-one (18.0 g, 0.082 mol, purity: 92.29) and 5% Pd/C (0.18 g) were placed in a 100 ml autoclave, and the reaction was allowed to proceed at 100° C. for 4 hours under a hydrogen pressure of 2.5 MPa. After cooling to room temperature, the catalyst was filtered off, and the obtained crude product was purified by silica gel chromatography (hexane ethyl acetate=19/1) to obtain (1'R)-4-methyl-6-(2,2,3-trimethylcyclopentan-1-yl)-3-hexanone (14.8 g, 0.066 mol) as a colorless oily substance. Percentage yield: 88%. The optical purity was 82% e.e.

GC/MS (m/e): 224 (M$^+$, 2%), 223 (7%), 206 (2), 191 (3), 177 (7), 167 (1), 137 (4), 123 (4), 99 (12), 86 (100), 83 (12), 57 (45), 55 (20), 41 (25);

$^1$H NMR (CDCl$_3$, 500 MHz) δ 0.48 (d, 3H, J=6.5 Hz), 0.82 (dd, 3H, J=6.9, 1.4 Hz), 0.84 (s, 3H), 0.88-1.02 (m, 1H), 1.05 (dd, 3H, J=7.3, 1.2 Hz), 1.07 (t, 3H, J=6.5 Hz), 1.10-1.25 (in, 3H), 1.27-1.41 (m, 2H), 1.43-1.57 (m, 2H), 1.66-1.85 (m, 2H), 2.41-2.48 (m, 2H), 2.49-2.55 (m, 1H);

$^{13}$C NMR (CDCl$_3$, 500 MHz) δ 215.55, 215.53, 51.01, 50.75, 46.55, 46.40, 45.20, 42.28, 34.19, 34.09, 32.55, 32.25, 30.08, 28.24, 28.18, 28.16, 28.04, 25.65, 25.63, 16.77, 16.18, 14.35, 13.83, 7.85, 7.80;

IR (ATR, diamond cell was used, cm$^{-1}$): 2937, 2868, 1713, 1459, 1376, 1365, 1104, 973.

Odor description: powdery, musk, woody, and citrus

Example 5: Evaluation of Odor Quality

The compound synthesized in Example 1 was each subjected to sensory evaluation. Ten professional panelists each having a five-year experience or more examined the quality of the odor. The results are shown in Table 1 below. This compound was excellent in diffusibility and had a strong musk odor with transparency, indicating that the compound is a useful compound.

TABLE 1

| | Structural formula | Odor description |
|---|---|---|
| Example 1 | (structure) | strong musk with diffusibility, transparent and warm odor |

Example 6: Fragrance Composition

A fragrance composition for perfume was prepared by using the compound synthesized in Example 1 above according to the following formula in Table 2.

TABLE 2

| Formula | (Parts by weight) |
|---|---|
| Allyl caproate | 14 |
| L-Citronellyl nitrile (manufactured by Takasago International Corporation) | 6 |
| CYCLAPROP (registered trademark) (manufactured by International Flavors & Fragrances) | 30 |
| α-Damascone | 12 |
| Ethyl 2-methylbutyrate | 10 |
| Ethyl methylphenylglycidate | 8 |
| Eugenol | 2 |
| FRUITATE (registered trademark) (manufactured by Kao Corporation) | 10 |
| Geranyl acetate | 16 |
| HEDIONE (registered trademark) (manufactured by Firmenich) | 100 |
| HELIOBOUQUET (registered trademark) (manufactured by Takasago International Corporation) | 6 |
| cis-3-Hexenol | 2 |
| Hexyl acetate | 30 |
| Hexyl cinnamic aldehyde | 70 |
| Hexyl salicylate | 50 |
| HINDINOL (registered trademark) (manufactured by Takasago International Corporation) | 8 |
| cis-Jasmone | 1 |
| Linalyl acetate | 10 |
| Orange oil | 50 |
| L-ORANTHA SUPER (registered trademark) @ 1.0% in DPG (manufactured by Takasago International Corporation) | 6 |
| ORBITONE (registered trademark) (manufactured by Takasago International Corporation) | 20 |
| PEONILE (registered trademark) (manufactured by Givaudan) | 14 |
| PHENOXANOL (registered trademark) (manufactured by International Flavors & Fragrances) | 20 |
| Raspberry ketone | 36 |
| ROSYPANE SUPER @ 1.0% in DPG (manufactured by Givaudan) | 4 |
| Tetrahydrolinalool | 100 |
| TRIPLAL (registered trademark) (manufactured by International Flavors & Fragrances) | 4 |
| γ-Undecalactone | 20 |
| VERDOX (manufactured by International Flavors & Fragrances) | 60 |
| Yara yara | 2 |
| Dipropylene glycol | 209 |
| Compound of Example 1 | 70 |
| Total | 1000 |

Sensory evaluation was carried out by four professional panelists each having a five-year experience or more. All the four panelists stated that the fragrance composition containing the compound of Example 1 hand having a fruity-floral note had bright and soft odor with good diffusibility, was highly preferable, and was excellent in odor quality.

Example 7: Liquid Detergent

A liquid detergent (100 g) scented with the above-described fragrance composition of the Example 6 at 0.5% was prepared according to the formula in Table 3 below. Sensory evaluation of this liquid detergent was carried out by four professional panelists each having a five-year experience or more. All the four panelists stated that a bright, warm, and fruity-floral note was clearly recognizable, and that the liquid detergent was highly preferable and excellent in odor quality.

TABLE 3

| Formula (Components) | (Formulated amount g) |
|---|---|
| Polyoxyalkylene alkyl ether | 50.00 |
| Water | 35.13 |
| Butyl CARBITOL | 8.00 |
| Linear alkyl benzenesulfonic acid salt | 2.50 |
| p-Toluenesulfonic acid | 1.00 |
| Polyethylene glycol | 1.00 |
| Monoethanolamine | 1.00 |
| Coconut oil fatty acid | 0.10 |
| Citric acid | 0.22 |
| Sodium benzoate | 0.50 |
| BHT | 0.05 |
| Fragrance composition of Example 6 | 0.50 |
| Total | 100.00 |

Example 8: Shampoo

A shampoo (100 g) scented with the above-described fragrance composition of the Example 6 at 1.0% was prepared according to the formula in Table 4 below. Sensory evaluation of this shampoo was carried out by four professional panelists each having a five-year experience or more. All the four panelists stated that the shampoo was highly preferable and excellent in odor quality.

TABLE 4

| Formula (Components) | (Formulated amount g) |
|---|---|
| Sodium polyoxyethylene lauryl ether sulfate | 14.00 |
| Lauramidopropyl betaine | 4.00 |
| Coconut oil fatty acid diethanol amide | 3.00 |
| Cationic cellulose | 0.50 |
| Ethylene glycol distearate | 1.00 |
| Ethyl paraoxybenzoate | 0.25 |
| Citric acid | quantum sufficit |
| Fragrance composition of Example 6 | 1.00 |
| Purified water | the balance |
| Total | 100.00 |

Example 9: Body Wash

A body wash (100 g) scented with the above-described fragrance composition of Example 6 at 0.95% was prepared according to the formula in Table 5 below. Sensory evaluation of this body wash was carried out by four professional panelists each having a five-year experience or more. All the four panelists stated that a bright fruity-floral note was clearly recognizable, and the body wash was highly preferable and excellent in odor quality.

TABLE 5

| Formula (Components) | (Formulated Amount g) |
|---|---|
| Triethanolamine | 9.00 |
| Lauric acid | 6.00 |
| Myristic acid | 9.00 |
| Disodium laureth sulfosuccinate (1 E.O.) (42%) | 10.00 |
| (C8-16)Alkyl glucosides | 8.00 |
| Glyceryl laurate | 1.00 |
| 2-Hydroxyethyl distearate | 2.50 |
| Coconut oil fatty acid diethanolamide | 3.00 |
| Propylene glycol | 5.00 |
| Dibutylhydroxytoluene | 0.05 |
| Disodium edetate | 0.10 |
| Ethyl paraoxybenzoate | 0.20 |
| Methyl paraoxybenzoate | 0.10 |
| Fragrance composition of Example 6 | 0.95 |
| Purified water | the balance |
| Total | 100.00 |

Comparative Example 1: Comparison of Odor Quality Based on Difference in Optical Purity Regarding Configuration at 1'-Position Optically active materials obtained by mixing optically active (1'R)- and (1'S)-3-methyl-5-(2,2,3-trimethylcyclopentan-1-yl)-2-pentan ones at various ratios were subjected to sensory evaluation, and were compared with one another in terms of the difference in quality of odor. The evaluation was carried out by ten professional panelists each having a five-year experience or more. The results are shown in Table 6 below. Based on the evaluation, the material showed a better and stronger musk odor with a higher transparency, as the optical purity of the (1°R)-isomer regarding the configuration at 1'-position, got higher.

TABLE 6

| Optical purity % e.e. | (R)/(S) wt % | Odor quality | Musk intensity |
|---|---|---|---|
| 20(R) | 60/40 | musk with fruity nuance and woody nuance | strong |
| 40(R) | 70/30 | musk, fruity, faintly woody-like odor | strong |
| 50(R) | 75/25 | musk with slightly fruity nuance | strong |
| 60(R) | 80/20 | strong musk, floral | very strong |
| 70(R) | 85/15 | strong musk with slight floral note | very strong |
| 82(R) (Example 1) | 91/9 | strong musk with transparency and warmth | very strong |
| 98(R) | 99/1 | strong musk, transparent and elegant odor | very strong |
| 10(R) | 55/45 | slightly weak musk with fruity nuance | weak |
| 0 | 50/50 | fruity, woody | very weak |
| 20(S) | 40/60 | woody, fruity | very weak |
| 40(S) | 30/70 | woody with fruity nuance | very weak |
| 56(S) (Example 2) | 22/78 | woody with fruity nuance, faintly metallic | very weak |

Musk intensity:
Very Strong: strong and distinct musk odor
Strong: distinct musk odor
Weak: faint musk odor
Very Weak: no musk odor

The invention claimed is:

1. A compound of the following formula (A):

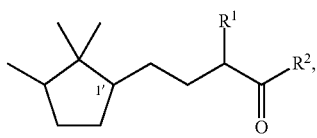

wherein 1'-position is optically active; and one of $R^1$ and $R^2$ is a methyl group and the other represents an ethyl group, or both $R^1$ and $R^2$ are a methyl group;
wherein the optical purity regarding a configuration at 1'-position is in a range from 20% e.e. to 99% e.e; and
wherein an R-isomer is in excess regarding the optical activity at 1'-position in the formula (A).

2. The compound according to claim 1, wherein $R^1$ and $R^2$ are methyl groups.

3. A fragrance composition, comprising the compound of formula (A) according to claim 2.

4. A method for augmenting or modifying an odor of a fragrance composition, the method comprising adding the compound according to claim 2.

5. The compound according to claim 1, wherein one of $R^1$ and $R^2$ is a methyl group, and the other is an ethyl group.

6. A fragrance composition, comprising the compound of formula (A) according to claim 5.

7. A method for augmenting or modifying an odor of a fragrance composition, the method comprising adding the compound according to claim 5.

8. An optically active (1'R)-3-methyl-5-(2,2,3-trimethyl-cyclopentan-1-yl)-2-pentanone,
wherein the optical purity regarding a configuration at 1'-position is in a range from 60% e.e. to 99% e.e.

9. A fragrance composition, comprising the compound of formula (A) according to claim 8.

10. A method for augmenting or modifying an odor of a fragrance composition, the method comprising adding the compound according to claim 8.

11. (1'R)-3-Methyl-5-(2,2,3-trimethylcyclopentan-1-yl)-2-pentanone.

12. A fragrance composition, comprising the compound of formula (A) according to claim 1.

13. A product scented with the fragrance composition according to claim 12.

14. The scented product according to claim 13, which is one selected from fragrance products, cosmetics, basic skin care cosmetics, make-up cosmetics, hair cosmetics, sunscreen cosmetics, medicated cosmetics, hair-care products, soaps, body cleaning agents, bath agents, laundry detergents, finishing softeners for clothes, cleaning agents, kitchen detergents, bleaching agents, aerosols, air fresheners, repellents, and groceries.

15. The fragrance composition according to claim 12, wherein
the content of the compound of formula (A) is 0.01 to 60% by weight.

16. The fragrance composition according to claim 12, wherein
the chemical purity of the compound is 80% or higher.

17. A method for augmenting or modifying an odor of a fragrance composition, the method comprising adding the compound according to claim 1.

* * * * *